United States Patent [19]

Van Ness et al.

[11] Patent Number: 5,390,792
[45] Date of Patent: Feb. 21, 1995

[54] STERILE PACKAGING

[75] Inventors: William Van Ness, Flemington; Robert J. Kalinski, Milford, both of N.J.

[73] Assignee: Ethicon, Inc., Somerville, N.J.

[21] Appl. No.: 139,599

[22] Filed: Oct. 18, 1993

[51] Int. Cl.⁶ ............... B56D 81/02; A61B 19/02
[52] U.S. Cl. .................. 206/439; 206/213.1; 206/587; 206/815
[58] Field of Search ............ 206/439, 213.1, 587, 206/815

[56] References Cited

U.S. PATENT DOCUMENTS

| | | | |
|---|---|---|---|
| 4,466,552 | 8/1984 | Butterworth et al. | 206/439 |
| 4,664,256 | 5/1987 | Halskov | 206/213.1 |
| 5,052,558 | 10/1991 | Carter | 206/439 |
| 5,217,118 | 2/1993 | Mochizuki et al. | 206/587 X |
| 5,246,109 | 9/1993 | Markle et al. | 206/439 X |

FOREIGN PATENT DOCUMENTS

| | | | |
|---|---|---|---|
| 1192525 | 8/1985 | Canada | 206/439 |
| 2904042 | 8/1980 | Germany | 206/587 |

*Primary Examiner*—William I. Price
*Attorney, Agent, or Firm*—Emil Richard Skula

[57] ABSTRACT

A packaging for the protective sterile containment of a rigid product and, more particularly, a sealed container protectively enclosing the sterile product, such as a liquid-filled vial, during shipment and handling of the packaging, and upon opening of the packaging in a sterile environment; for instance, a surgical operating room, facilitating the sterile transfer of the product from the packaging into the sterile environment. The packaging includes a substantially rigid, resiliently flexible thermoformed plastic container having a plurality of indentations or recessed wall portions molded or thermoformed into various of the side, end and bottom wall surfaces of the container, with such wall portions forming contacting surfaces shaped in correlation with the exterior surface portions of a product housed in the container so as to position the product therein in a specified orientation, and in which at least one of the indentations includes product-gripping structure protectively maintaining the product within the packaging container in its fixed position during shipping and handling of the container so as to be secure from potential damage due to impacts or shocks imparted to the packaging. The indentations are formed with venting ridges constituting tubular passages between the mutually contacting surfaces of the container and the product to enable an improved and substantially unhindered circulation of sterilizing gases throughout the interior of the packaging and about the product.

7 Claims, 2 Drawing Sheets

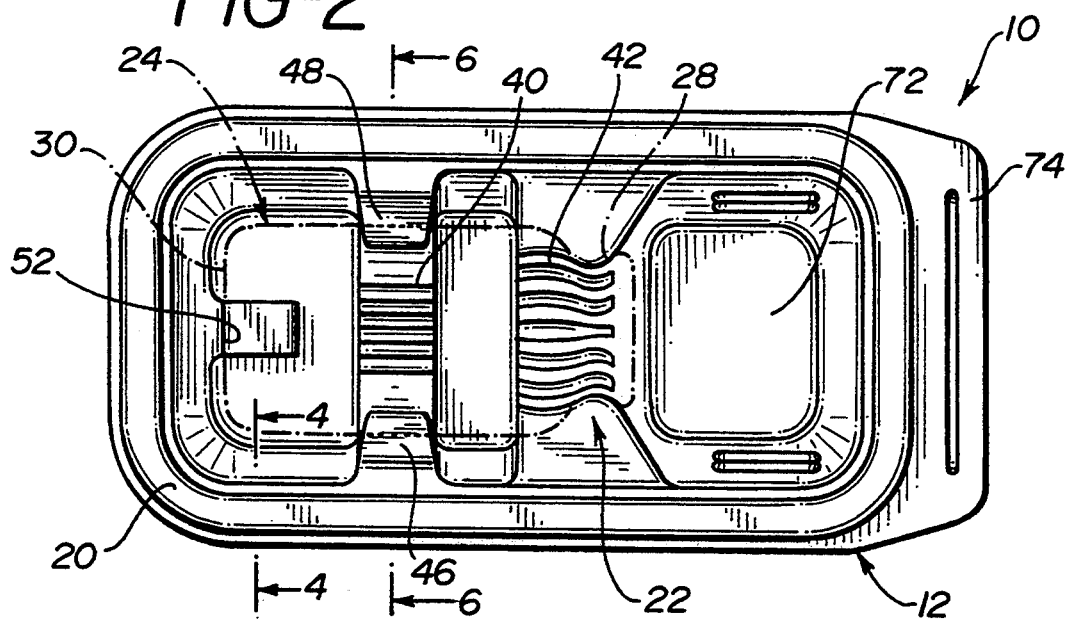
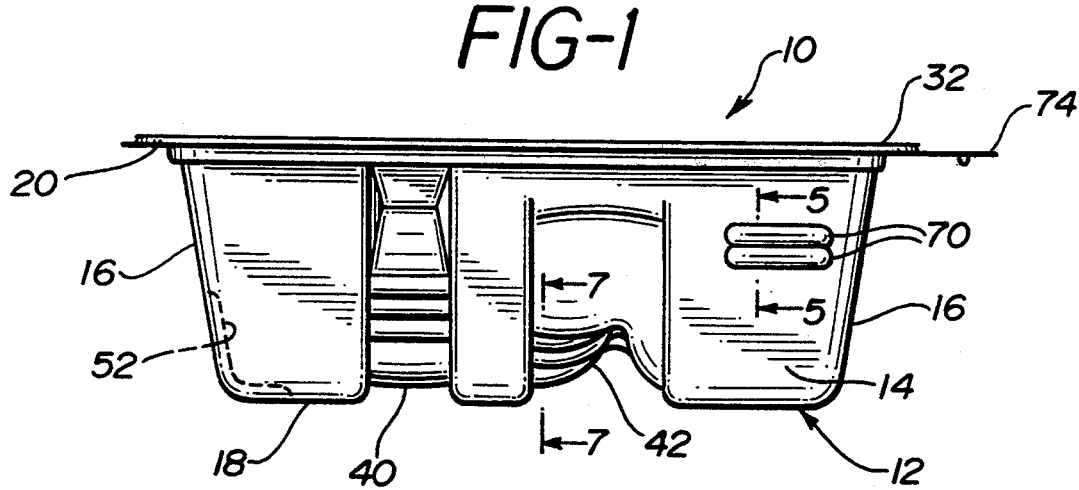
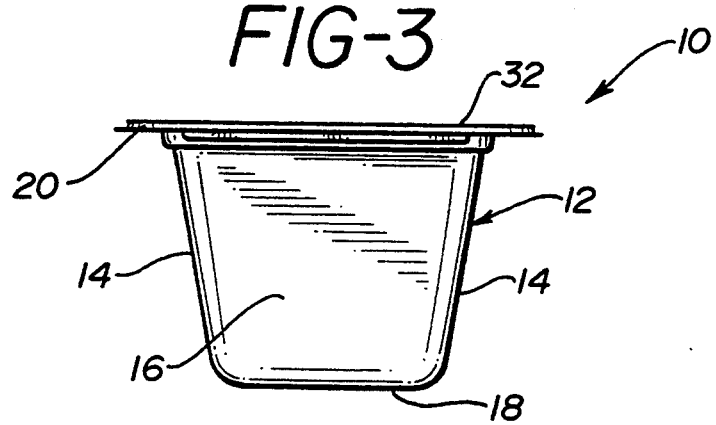

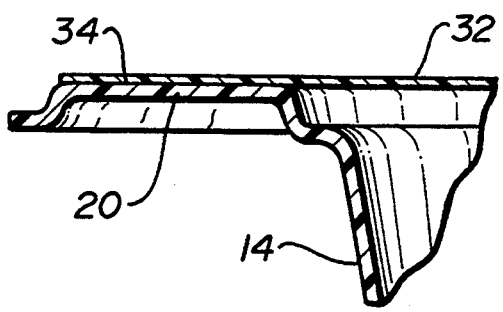
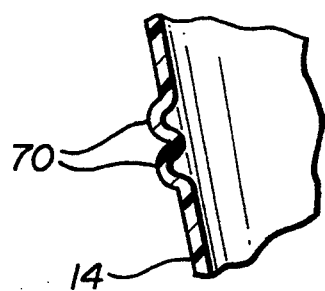
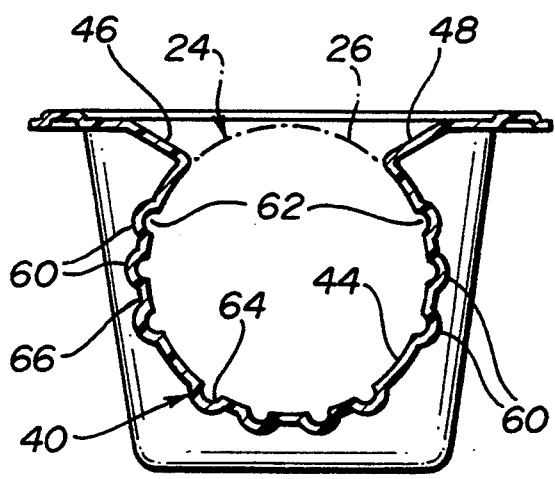
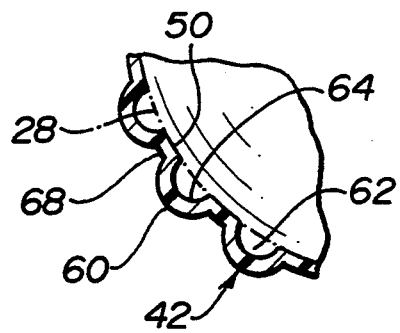
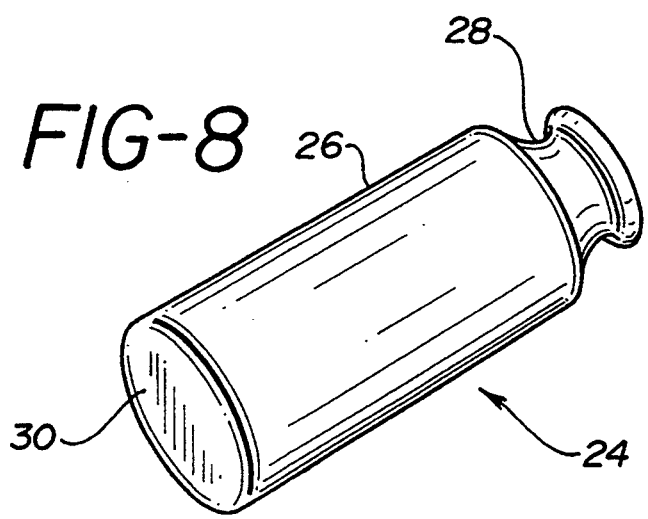

STERILE PACKAGING

BACKGROUND OF THE INVENTION

1. Field of the Invention

The present invention relates to a packaging for the protective sterile containment of a rigid product and, more particularly, relates to a sealed container protectively enclosing the sterile product, such as a liquid-filled vial, during shipment and handling of the packaging, and upon opening of the packaging in a sterile environment; for instance, a surgical operating room, facilitating the sterile transfer of the product from the packaging into the sterile environment.

2. Discussion of the Prior Art

The protective containment or packaging of a sterile product, such as a liquid-filled vial which is to be removed from the packaging and the contents thereof dispensed in a sterile environment may entail the provision of a packaging including a substantially rigid resiliently flexible thermoformed plastic container which incorporates therein a clampingly engaging support for the product, and whereby the product-containing container is sealed through the application of a covering comprising a suitable plastic film material to formulate the complete packaging. In connection with the foregoing, the interior of the product-containing packaging is ordinarily sterilized through the circulation therethrough of a suitable gaseous sterilizing medium in order to maintain the product, such as the liquid-filled vial, in a sterile condition during shipping and handling of the packaging, and also during the product being dispensed from the packaging into a sterile environment. For this purpose, the container constituent of the packaging, the latter of which is generally referred to as a "blister package", is formed from a rigid resiliently flexible thermoformed plastic material, preferably polypropylene, which will retain its shape during the sterilizing of the interior thereof with a sterilizing medium, and which concurrently incorporates internal structure adapted to position and grippingly engage the rigid product contained therein so as to maintain the product in a fixed position within the container for its protection during shipping and handling of the packaging. The product-containing container is normally sealed through the superposition of a plastic film which may be heat-sealed to the container and is peelable therefrom when it is desired to gain access to and remove the product from the container, possibly in a sterile environment.

Frequently, packaging including containers of this type and forming so-called blister packages, are thermoformed from a suitable plastic material, as mentioned preferably such as polypropylene, which will maintain its configurational integrity and structural rigidity during sterilizing of the interior of the product-containing container, for example, through the intermediary of sterilizing gases consisting, by of example, of either ethylene oxide, hydrogen peroxide or steam, and in which the exterior surfaces of the rigid product housed in the packaging, for instance, such as a liquid-filled vial, are sterilized by means of the sterilizing gas which is circulated through the packaging.

Although it is well known in the packaging technology to produce protective packaging structures, such as in the shape of plastic blister packages or the like, for protectively housing sterile products, such as surgical and/or medical implements, or liquid-filled vials which are to be ultimately removed from the packaging in a sterile environment; for example, in a surgical operating room, an important aspect in improving such packages resides in minimizing the contact surface areas between the internal wall surfaces of the container and the exterior surfaces of the product to facilitate an essentially unhindered circulation of the sterilizing gas within the packaging about the surfaces of the product. Furthermore, it is also significant to be able to configure the container so as to facilitate the easy sterile removal of the product from the packaging container with minimum expenditure of effort and ease in handling or manipulation subsequent to peeling the protective sealing film from the container.

SUMMARY OF THE INVENTION

Accordingly, the invention provides for a novel sterile packaging structure of the so-called blister package type, including a rigid resiliently flexible thermoformed plastic container having a plurality of indentations or recessed wall portions molded or thermoformed into various of the side, end and bottom wall surfaces of the container, with such wall portions forming contacting surfaces shaped in correlation with the exterior surface portions of a product housed in the container so as to position the product therein in a specified orientation, and in which at least one of the indentations includes product-gripping structure protectively maintaining the product within the packaging container in its fixed position during shipping and handling of the container so as to be secure from potential damage due to impacts or shocks imparted to the packaging.

Furthermore, an aspect of the invention resides in the indentations formed therein, and the interior surfaces of which contact the rigid product or liquid-filled vial, to be equipped or molded with venting ridges or ribs forming essentially tubular passages between the mutually contacting surfaces of the container and the product to enable an improved and substantially unhindered circulation of sterilizing gases throughout the interior of the packaging and about the product. In effect, the venting ridges or ribs in the indentations forming the tube-like passages in conjunction with the contacting surface portions of the product also concurrently reduce the extent of contact area which is present between the product and the interior wall surfaces of the container of the blister package.

Furthermore, the container wall structure of the blister package is disposed to have finger-gripping structure molded therein such that, upon peeling off of the sealing film covering the container, this will enable the relatively uncomplicated manual removal of the product from the container while holding the latter with one hand, and with the provision of an open head space in the container at one end of the product facilitating manual access to the product for sterile transfer into a sterile environment, such as a surgical operating room.

The container is formed with an integral peripheral flange structure about the rim thereof for enabling the adhesive sealing thereto of the covering film, the latter of which is preferably constituted from polyethylene fibers, in essence, a spun bonded olefin material, sold under the trademark Tyvek by the DuPont company, Wilmington Del., thereby effectively protectively enclosing the contents of the container. The flange structure may be provided with a raised planar surface portion extending about the perimeter thereof, so as to enlarge the sealing contact surface area between the covering film and the flange thereby enhancing upon the sealing action between the covering film and the container.

Accordingly, it is an object of the present invention to provide a novel and unique packaging of the blister package type for protectively storing a product in a sterile environment.

It is a more specific object of the present invention to provide a container constituted of a rigid resiliently flexible thermoformed plastic material which is adapted to protectively receive and clampingly engage a sterile product therein, and whereby the container is sealingly covered by a plastic film material.

Yet another object of the present invention is to provide a packaging of the type described, including a rigid resiliently flexible container having indentations formed in the walls thereof providing recessed wall portions constituting contact surfaces with the product for positioning the product in the container and for clampingly engaging the product in the container over minimum contact areas with the internal wall surfaces thereof so as to protect the product from damage during shipping and handling of the packaging.

A further object of the present invention is to provide a packaging of the type described wherein the indentations or recessed container walls which form contact surfaces with the product maintain the remaining surfaces of the product in spaced relationship with the wells of the container and include vent ridges or ribs forming tubular passages communicating surfaces of the product on opposite sides of the indentations, enabling an essentially unhindered circulation of sterilizing gases throughout the interior of the packaging and about the product contained in the packaging.

A still further object of the present invention is to provide for a generally rigid resiliently flexible thermoformed plastic container protectively housing a rigid sterile product, such as a liquid-filled vial, and including a peelable covering film sealed to and closing the container, whereby the covering film may be removed in a sterile environment allowing for the sterile removal of the product from the container.

BRIEF DESCRIPTION OF THE DRAWINGS

Reference may now be had to the following detailed description of an exemplary embodiment of a sterile packaging constructed pursuant to the invention, taken in conjunction with the accompanying drawings; in which:

FIG. 1 illustrates a side view of a sterile packaging constructed pursuant to the invention for protectively enclosing a product, such as a liquid-filled vial, in a sterile environment;

FIG. 2 illustrates a top plan view of the packaging with the covering film for sealingly closing the product-receiving container shown as having been peeled off therefrom for purposes of clarity of representation;

FIG. 3 illustrates an end view of the packaging container;

FIG. 4 illustrates a fragmentary sectional view, shown on an enlarged scale, taken along line 4—4 in FIG. 2;

FIG. 5 illustrates a fragmentary sectional view, shown on an enlarged scale, taken along line 5—5 in FIG. 1;

FIG. 6 illustrates a transverse sectional view taken along line 6—6 in FIG. 2;

FIG. 7 illustrates a fragmentary sectional view, shown on an enlarged scale, taken along line 7—7 in FIG. 1; and FIG. 8 illustrates a perspective view of a product in the shape of a liquid-filled cylindrical vial which is adapted to be protectively housed in the packaging of the invention.

DETAILED DESCRIPTION OF THE PREFERRED EMBODIMENT

Referring now in more specific particularity to the drawings, and especially FIGS. 1 through 3, there is illustrated an inventive packaging 10 for the protective and sterile containment of a product, for example, such as a rigid and essentially cylindrical liquid-filled vial, the contents of which are adapted to be employed in medical or surgical applications in a sterile field.

In essence, as shown in FIG. 1, the packaging 10, which is generally referred to as a blister package, includes a rigid resiliently flexible container 12, preferably constituted of thermoformed polypropylene. The container 12 has sidewalls 14, end walls 16 and a substantially flat bottom wall 18 so as to define a substantially rectangular tub-like configuration. The sidewalls 14 and end walls 16 extend upwardly and outwardly angled from the perimeter of bottom wall 18 and, at their upper ends defining the rim of the container, extend into a generally planar horizontally outwardly projecting flange structure 20 which encompasses the confines of the container 12.

The container walls 14, 16 and 18 collectively define a well or container interior 22 adapted to receive and protectively house a product 24 in a sterile environment; for example, a product such as a liquid-filled vial 24 which, as shown in FIG. 8, includes a cylindrical body 26 extending at one end thereof into a reduced neck portion 28 having a liquid dispensing beaded opening or lip, and at the opposite end having a generally flat or slightly recessed bottom 30. The vial 24 may consist of glass and contain suitable liquids which are to be dispensed therefrom in a sterile medical or surgical environment.

As shown in the drawings, the height of the sidewalls 14 and end walls 16 of the container 12 is sufficient to cause the vial 24 to be contained within the well 22 so as to be positioned below a plane defining the upper surface of the flange structure 20, and thereby avoiding physical contact with a covering film 32 which is preferably heat-sealed to the upper flange surface area of the container 12.

In order to increase the strength and efficiency of the seal which is present between the covering film 32 and the container 12, as is clearly shown by the sectional representation of FIG. 4, the upper surface of the flange structure 20 is configured to include a raised planar surface portion 34 extending about the container 12. This surface position 34 increases the surface area of the flange structure 20 contacting that of the superimposed covering film 32 and, consequently, renders available a larger sealing area for the implementation of an effective and strong heat seal between the covering film 32 and container 12.

Preferably, in order to enable sterilizing the interior of the packaging 10 as described in further detail hereinbelow, the covering film 32 is produced from polyethylene fibers, and particularly spun bonded olefin which is sold under the registered trademark Tyvek by the DuPont Company, Wilmington Del. The film material is resistant and inert to attack from most chemicals, including normally employed sterilizing gases, and is breathable to enable such sterilizing gases to permeate therethrough, however, while being essentially impervious to airborne bacteria and viruses. Moreover, the film material can be readily adhesively fastened, such as by heat sealing, to the polypropylene material of the container 12.

In order to retain the product 24; in effect, the liquid-filled vial, in a secure position within the container 12 so as to protect the product from damage during handling of the packaging 10, the sidewalls 14, at least one end wall 16 and bottom wall 18 are provided with suitable indentations-or contourings forming recessed wall portions therein, as described more specifically hereinbelow.

Thus, in the instance where the product which is to be protected in a sterilized environment within the packaging 10 consists of the vial 24 possessing a cylindrical body 26 and having the reduced neck end 28 at one end thereof, in order to precisely position and clampingly support the vial 24 within the container 12, mutually spaced indentations forming inwardly recessed wall portions 40 and 42 are integrally molded or formed into the bottom wall 18 and sidewalls 14, axially spaced from each other along the length of bottom wall 18, as shown in FIGS. 1 and 2 of the drawings.

The indentation 40, as illustrated in the cross-sectional representation of FIG. 6, is a part annularly extending, circularly shaped indentation in the side and bottom walls 14, 18, the diameter of the inner surface of which substantially conforms to the diameter or curvature of the cylindrical body 26 of vial 24, and which encompasses somewhat more than one-half the circumferential extent of the cylindrical portion 26 of the vial 24 when the latter is positioned in the container 12. Hereby, the inner surface 44 of the indentation 40 terminates at opposite ends 46, 48 into structure which somewhat more narrowly spaced from each other than the diameter 26 of vial 24 so as to, upon insertion of the vial 24, and in conjunction with the curved surface 44, form a clamping support about the cylindrical portion 26 of vial 24 across the width of indentation 40.

The indentation or inwardly extending wall recess 42 is configured so as to complementarily conform with the shape of the neck portion 28 of vial 24 so as to cause the neck portion 28 to contact against the inner curvilinear surface 50 in a manner in which it will inhibit axial displacement of the vial 24 within container 12 towards the one end wall 14 facing the head or neck end 28 of the vial 24; whereas an inward depression or indentation 52 which is centrally formed in the opposite end wall 14 and bottom wall 18 forms an end stop against which there rests the bottom or base end 30 of the vial 24, thereby essentially restraining the vial 24 within the container 12 against displacement thereof in any direction.

The provision of the inwardly depending recesses or indentations 40, 42 and 52 which enable the positioning and clamping fast of the vial 24 within the well 22 or confines of the container 12 ensure that the remaining external surface portions of the vial 24 which do not contact the contiguous surfaces of the indentations are maintained-in a spaced or raised away relationship from the internal wall surfaces of the container 12 so as to enable a circulating flow of sterilizing gases about the vial 24 during sterilizing of the interior confines of the packaging 10 when sealed by the covering film 32.

The circulation of any gaseous sterilizing medium within the packaging 10 and about the surfaces of vial 24 is inventively improved upon by the incorporation of a plurality of spaced and longitudinally extending and in cross-section outwardly curved ridges or ribs 60 forming tube-like passages 62 in the interiorly facing surfaces across each of the respective indentations 40 and 42 and communicating the opposite sides of each of these indentations with the adjacent spaces in the container 12 when the vial 24 is positioned therein. These passages 62 extending across the width of each of the inner surfaces 64 of indentations 40, 42, and in addition to aiding in the circulation of the sterilizing gas or medium within the packaging 10, also concurrently reduce the contacting surface areas between the vial 24 and the adjacently located surfaces of the container 12 supporting the vial.

The indentations 40 and 42 are also adapted to have their respective external recessed surfaces 66 and 68 serve as finger gripping means adapted to assist in grasping and holding the packaging 10. Moreover, the opposite sidewalls 14 may each have elongated projecting ridges or ribs 70 thermoformed or molded therein, with such ridges also serving as finger gripping structure to enable secure manual holding of the packaging 10 during the stripping off of the covering film 32 from the flange structure 20 on the container 12 in order to facilitate access to and removal of the product or vial 24 from the container.

The one end 72 of the interior portion of the container 12 may be dimensioned to extend beyond the neck end 28 of the vial 24 mounted therein so as to provide adequate space between the vial 24 and the facing end wall 16 of the container to enable insertion of the finger of a user beneath the neck portion 28 and afford an easy grasping of the vial for pulling the latter out of the container 12 subsequent to the stripping off of the plastic covering film 32. To render this stripping easier, an extension or lip 74 may be integrally formed with the flange structure 20 at that end, over which there extends one end of the film. This film end can then be readily gripped by the fingers of one hand of the user while holding the container 12 with the other hand, while grasping the indentions 40 or 42 for support, and then pulling the covering film 32 off the container 12 to expose the product or vial 24.

The vial 24 is normally maintained in a sterile condition within the sealed packaging 10 inasmuch as the interior of the latter is sterilized by means of a gaseous sterilizing medium, preferably such as hydrogen peroxide, ethylene oxide or steam, whereby the covering film 32 is permeable to the sterilizing medium to enable passage of the latter therethrough.

In summation, the packaging 10 for the protection of the sterile product, in effect, the blister package design pursuant to the invention, provides for a superior protective containment of a product, such as a liquid-filled vial, during shipment and handling thereof, and with the internal passages in the walls of the container 12 enabling sterilizing by means of a circulating gaseous medium interiorly of the package while enabling easy and secure manipulation for sterile transfer of the product upon opening of the packaging in a sterile environment; for example, such as a surgical operating room.

The additional space 72 provided within the container 12 proximate the neck or head end 28 of the vial 24 provides clearance for manual engagement of the vial for extraction thereof from the opened container. Hereby, the external surfaces of the indentations 40 and 42, and also the ribs 70 in sidewalls 14 may serve as finger-grippable surfaces facilitating holding of the container during removal of the vial 24 therefrom.

Moreover, the raised sealing surface formed on the encompassing flange structure 20 of the container 12 adds strength to the flange structure, and concurrently improves upon the flatness of the sealing contact surface between the flange and the superimposed heat-sealed covering film material so as to also improve upon the quality in the heat seal of the packaging. Additionally, the flange structure prevents warpage of the container 12 when the interior thereof is sterilized with hot steam, or when heated for sealing on of the covering film 32.

While there has been shown and described what is considered to be a preferred embodiment of the invention, it will, of course, be understood that various modifications and changes in form or detail could readily be made without departing from the spirit of the invention. It is, therefore, intended that the invention be not limited to the exact form and detail herein shown and described, nor to anything less than the whole of the invention herein disclosed as hereinafter claimed.

What is claimed is:

1. A packaging for the protective sterile containment of a rigid product, and packaging comprising a self-supporting substantially rigid and resiliently flexible container including a bottom wall, sidewalls and end walls integrally formed with and extending upwardly from said bottom wall for containment of said product;

indentations formed in at least some of said walls for engaging external surface portions of said product and positioning said product within said container, at least some of said product surface-engaging wall indentations incorporating rib structure forming passages enabling the circulation of sterilizing fluids about the surface of said product; and, covering film means being sealed to the upper peripheral edges of said upstanding walls to sealingly enclose the product in said packaging, wherein a peripheral horizontally extending flange is formed to extend about the upper edges of said upstanding walls, said flange including a sealing surface for adhesive sealing engagement with said covering film means, wherein said sealing surface on said flange includes a raised planar surface portion for increasing the sealing surface area contacting said covering film means, wherein said covering film means comprises a heat sealable breathable plastic film, wherein said plastic film is constituted of polyethylene, wherein said container is substantially rectangular, said bottom wall being flat and said sidewalls and end walls extending upwardly angled from the edges of said bottom wall to form said product-receiving containment structure, and, wherein a first one of said indentations forms a first support for said product extending between said sidewalls and said bottom wall; a second said indentation forms a second support for said product extending between one said end wall and said bottom wall; and a third said indentation forms means for clampingly engaging said product extending between said sidewalls and said bottom wall, said indentations collectively constituting abutments for positioning and retaining said product in said container in spaced relationship with the remaining bottom wall, sidewall and end wall surfaces.

2. A packaging as claimed in claim 1, wherein rib structure is formed in said first and third indentations so as to provide fluid-flow passages communicating with the interior regions of said container at opposite sides of each of said indentations.

3. A packaging as claimed in claim 1, wherein said indentations inhibit movement of the product positioned within said container.

4. A packaging as claimed in claim 1 wherein said product comprises a liquid-filled vial having a cylindrical body portion, said first and third indentations contacting circumferential surface portions of said vial and said second indentation contacting a bottom end and cylindrical body portion of said vial for positioning said vial within said container.

5. A packaging as claimed in claim 4, wherein said vial includes a reducing neck portion at one end of said cylindrical body portion opposite the bottom end of the neck portion of said vial and said third indentation comprising wall structure resiliently clampingly engaging the cylindrical surface of said vial.

6. A packaging as claimed in claim 5, wherein said passages in said indentations contacting the surface of said vail extend in the direction of the longitudinal axis thereof so as to communicate the space in said container on opposite sides of each of the indentations.

7. A packaging as claimed in claim 5 wherein said container is dimensioned to provide an interior space in said container at the neck end of said cylindrical vial to enable access thereto for sterile manual removal of said vial from said packaging.

* * * * *

UNITED STATES PATENT AND TRADEMARK OFFICE
CERTIFICATE OF CORRECTION

PATENT NO. : 5,390,792
DATED : February 21, 1995
INVENTOR(S) : William Van Ness
Robert J. Kalinski It is certified that error appears in the above-indentified patent and that said Letters Patent is hereby corrected as shown below:

Column 8 - Line 44

"vail" should be "vial"

Signed and Sealed this

Twenty-ninth Day of August, 1995

*Attest:*

BRUCE LEHMAN

*Attesting Officer*          *Commissioner of Patents and Trademarks*